US 6,245,013 B1

(12) United States Patent
Minoz et al.

(10) Patent No.: US 6,245,013 B1
(45) Date of Patent: Jun. 12, 2001

(54) AMBULATORY RECORDER HAVING SYNCHRONIZED COMMUNICATION BETWEEN TWO PROCESSORS

(75) Inventors: Alain Minoz, Broma (SE); Thorir Gunnarsson, Reykjavik (IS); Malcolm G. S. Williams, Stockholm (SE); Arch W. Butler, St. Louis Park, MN (US); Henrik E. Pedersen, Vanloese (DK)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/237,926

(22) Filed: Jan. 27, 1999

Related U.S. Application Data

(63) Continuation of application No. 09/210,567, filed on Dec. 14, 1998.

(51) Int. Cl.$^7$ .................................................. A61B 5/00
(52) U.S. Cl. ............................. 600/300; 128/920; 705/3; 600/361
(58) Field of Search .................................. 600/300, 301, 600/345, 361, 365, 481–486, 500–508, 529–532, 538, 544–545; 128/920–925; 705/2–3, 35

(56) References Cited

U.S. PATENT DOCUMENTS

| D. 396,037 | 7/1998 | Cappa et al. . |
|---|---|---|
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. . |
| 5,010,888 | 4/1991 | Jadvar et al. . |
| 5,012,411 | 4/1991 | Policastro et al. . |

(List continued on next page.)

FOREIGN PATENT DOCUMENTS 0 356 603    9/1988   (SE) .

*Primary Examiner*—Cary O'Connor
*Assistant Examiner*—Michael Astorino

(57) ABSTRACT

An ambulatory recording system for medical and especially diagnostic purposes is described having synchronized communication between two processors. The recorder features two processors which are of differing architectures—the first processor being a real time processor which handles the sampling function, the second processor being a non real time processor which handles the operating system function. The invention further includes a protocol for communication between the two processors which permits the two processors to have synchronized and reliable communication.

33 Claims, 11 Drawing Sheets

U.S. PATENT DOCUMENTS

| | | |
|---|---|---|
| 5,016,636 | 5/1991 | Kulakowski . |
| 5,042,481 | 8/1991 | Suziki et al. . |
| 5,072,458 | 12/1991 | Suzuki . |
| 5,086,778 | 2/1992 | Mueller et al. . |
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |
| 5,131,816 | 7/1992 | Brown et al. ............................ 417/2 |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |
| 5,226,431 | 7/1993 | Bible et al. . |
| 5,228,450 | 7/1993 | Sellers . |
| 5,238,001 | 8/1993 | Gallant et al. . |
| 5,261,401 | 11/1993 | Baker et al. . |
| 5,263,491 | 11/1993 | Thornton . |
| 5,273,033 | 12/1993 | Hoffman . |
| 5,292,344 | 3/1994 | Douglas . |
| 5,305,202 | 4/1994 | Gallant et al. . |
| 5,305,761 | 4/1994 | Byrne et al. . |
| 5,307,263 | 4/1994 | Brown . |
| 5,309,920 | 5/1994 | Gallant et al. . |
| 5,338,157 | 8/1994 | Blomquist . |
| 5,341,291 | 8/1994 | Roizen et al. . |
| 5,343,870 | 9/1994 | Gallant et al. . |
| 5,355,892 | 10/1994 | Saltzstein . |
| 5,368,562 | 11/1994 | Blomquist et al. . |
| 5,381,351 | 1/1995 | Kwong et al. . |
| 5,388,587 | 2/1995 | Knutsson et al. . |
| 5,411,022 | 5/1995 | McCue et al. . |
| 5,429,602 | 7/1995 | Hauser . |
| 5,431,634 | 7/1995 | Brown . |
| 5,432,698 | 7/1995 | Fujita . |
| 5,438,985 | 8/1995 | Essen-Moller . |
| 5,479,019 | 12/1995 | Gross . |
| 5,479,935 | 1/1996 | Essen-Moller . |
| 5,507,904 | 4/1996 | Fisher et al. . |
| 5,526,809 | 6/1996 | Fiddian-Green . |
| 5,545,183 | 8/1996 | Alman . |
| 5,607,460 | 3/1997 | Kroll . |
| 5,645,068 | 7/1997 | Mezack et al. . |
| 5,657,759 * | 8/1997 | Essen-Moller ....................... 600/300 |
| 5,701,894 * | 12/1997 | Cherry et al. ........................ 600/300 |
| 5,704,368 | 1/1998 | Asano et al. . |
| 5,704,890 | 1/1998 | Bliss et al. . |
| 5,749,907 | 5/1998 | Mann . |

* cited by examiner

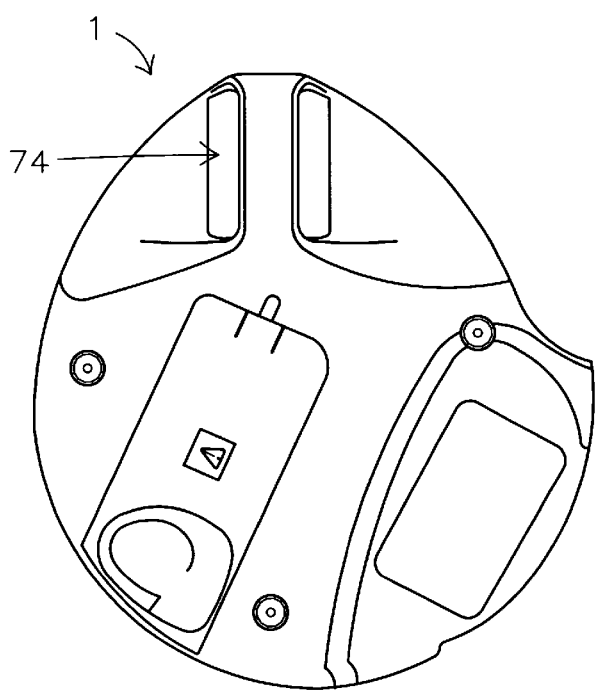
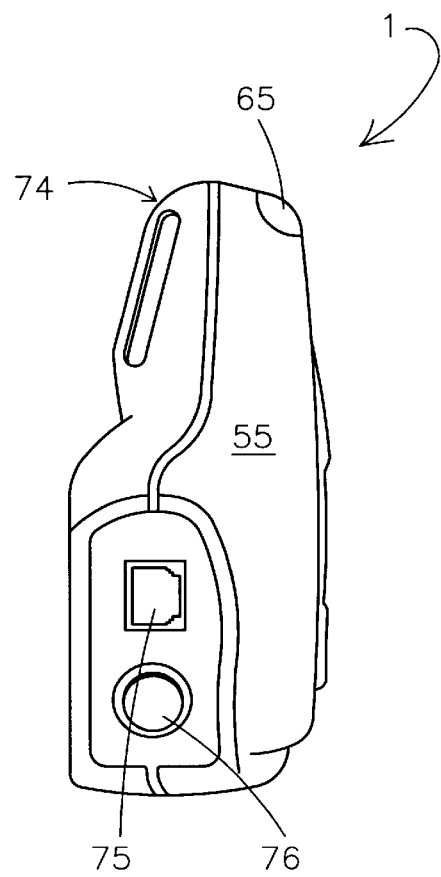
FIGURE 13  FIGURE 14

AMBULATORY RECORDER HAVING SYNCHRONIZED COMMUNICATION BETWEEN TWO PROCESSORS

"This is a continuation of copending application Ser. No. 09/210,567 filed on Dec. 14, 1998".

FIELD OF THE INVENTION

The present invention relates to ambulatory recording, of medical data especially for diagnostic purposes, and particularly to an ambulatory recorder having synchronized communication between two processors.

BACKGROUND OF THE INVENTION

Various physiologic signals are often recorded and analyzed. These signals may included digestive pH, various digestive motility and pressure signal, EEG and EMG, to list only a few.

Typically, physicians require the concurrent recording a variety of physiologic signals. For example, gastric pH is often collected at the same time as pressure. Through the concurrent collection of various parameters the physician may better understand the patient's condition.

Ambulatory recording and recorders are widely used to collect such data. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram), EEG (Electroencephalogram) or pH and pressure (Motility) in the gastrointestinal tract. Preferably such a recorder should be able to record among a programmable number of channels at a variety of programmable frequencies.

Among the problems with current recorders, however, is that of energy usage. Such recorders, because they must be ambulatory, are battery powered. Thus an ambulatory medical recorder must minimize energy usage while performing almost constant sampling across a variable number of channels at one or more frequencies. Besides minimizing energy usage, such recorders, however, must also offer robust functionality, i.e., be easy to operate, while also being flexible. Moreover, another crucial requirement is that such recorders be dependable, accurate and reliable.

One approach to construct a recorder offering flexible operation, ease of use, as well as a simple but powerful graphical user interface all while providing dependable, accurate and reliable data sampling and recording is through the use of two processors. This approach may include using processors of different types, such as the first processor being a real time processor ("NRTP") to handle the sampling function, while the second processor being a non real time processor ("NRTP") to handle the operating system function.

Among the problems with a data recorder using two processors is that of communication between the processors. Although this may be a problem regardless of the processors selected, in the situation where the first processor is a RTP and the second processor is a NRTP, the problem is especially acute. In particular, the RTP runs a real time single task software; while the NRTP runs a non-real time multitasking operating system and application with priorities. Thus, communication with the RTP could be started by several tasks within the NRTP at the same time. Ultimately this may lead to confusion in the recorder and ultimately lead to a system failure and/or data loss. Thus, there exists a need to ensure communication between two processors within an ambulatory recorder will be synchronized, thereby preventing system failure and/or data loss.

SUMMARY OF THE INVENTION

An ambulatory recording, for medical and especially for diagnostic purposes, and particularly to an ambulatory recorder having synchronized communication between a first processor and a second processor. In the preferred embodiment, the first processor is a real time processor ("RTP") which handles the sampling function, while the second processor is a non real time processor ("NRTP") which handles the operating system function. A protocol for communication between the two processors is provided which permits the processors to have synchronized and, therefore, reliable communication. The reliability aspect of the communication scheme is highly important since the sampled and stored data is the primary purpose of the data recorder. In the preferred embodiment the RTP operates only while sampling is occurring, while the NRTP only operates as needed. These as needed times include logging the sampled data into long term memory as well as reconfiguring system settings such as sampling frequency or channels to be sampled. In this manner an ambulatory medical recording device may be fashioned which has minimal power consumption but with reliable data acquisition and recording while still offering many features.

BRIEF DESCRIPTION OF THE DRAWINGS

FIG. 13 is a back view of the recorder shown in FIG. 2.

FIG. 14 is a side view of the recorder FIG. 2.

The FIGS. are not necessarily to scale.

DETAILED DESCRIPTION OF THE DRAWINGS

Figure 1A:
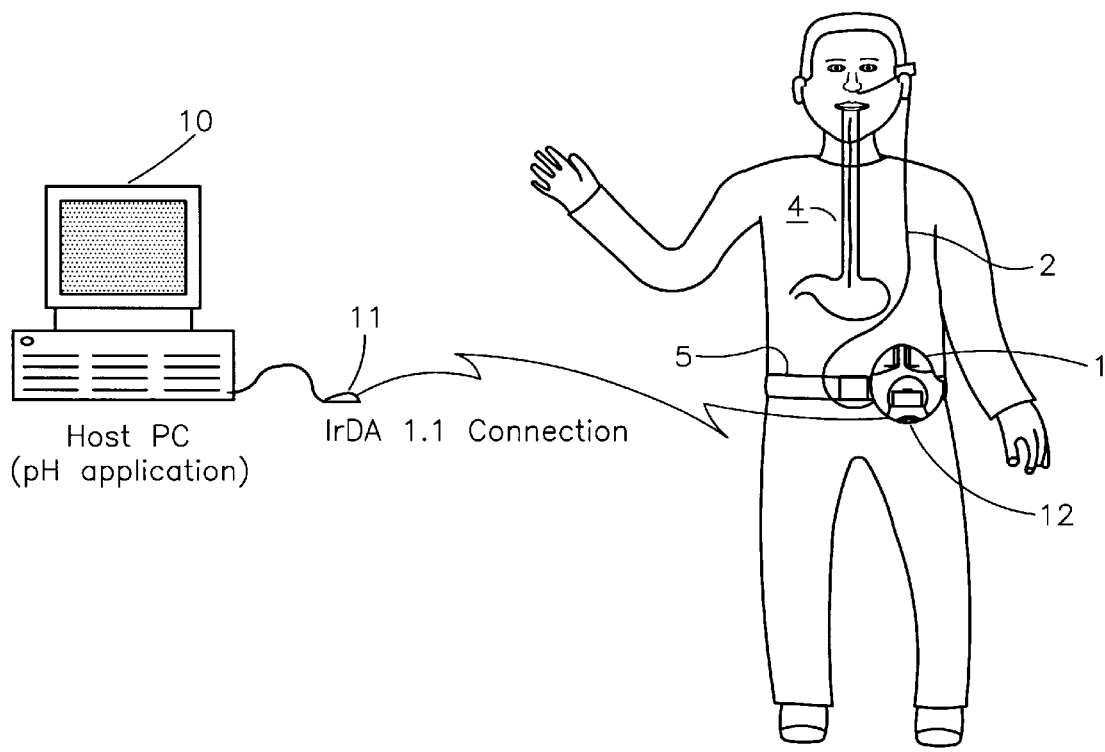
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body, from which data is to be sensed, including the esophagus, as depicted in this figure. It should be noted, that the ambulatory recorder of the present invention may be used to collect many or various types of data including gastrointestinal, neurological, as well as neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in FIG. 1A, recorder further permits two separate sensors to be coupled to the device, as seen in FIG. 1B.

As further seen in this figure, the recorder may also communicate with a host PC 10 via an infra red data link facility through an IrDA connection 11, for example, a JETEYE ESI-57680 available form Extended Systems, Inc., Boise, Id., which connects with the recorder using the infra Red Data Association 1.1 Connection Protocol. As seen, infra red data connection makes a link to infra red port 12 on recorder.

Figure 1B:
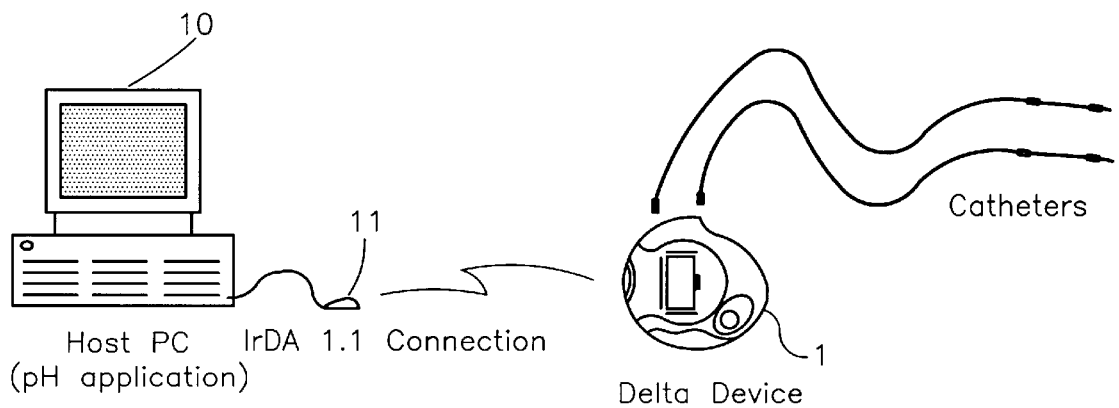
FIG. 1B illustrates a further manner in which the recorder 1 may also have an infra red data communication link made with a host PC.

FIG. 1B illustrates a further manner in which the recorder 1 may also have an infra red data communication link made with a host PC. In particular, the infra red data communication data recorder may be further made when the recorder is not worn by the patient. As discussed in more detail below, one of the advantages of the present invention is that the infra red data components and recorder case permits such a link to be made when the device is worn as shown in FIG. 1A as well as if the device is merely removed from the patient and positioned in proximity to mouse 11.

Figure 2:
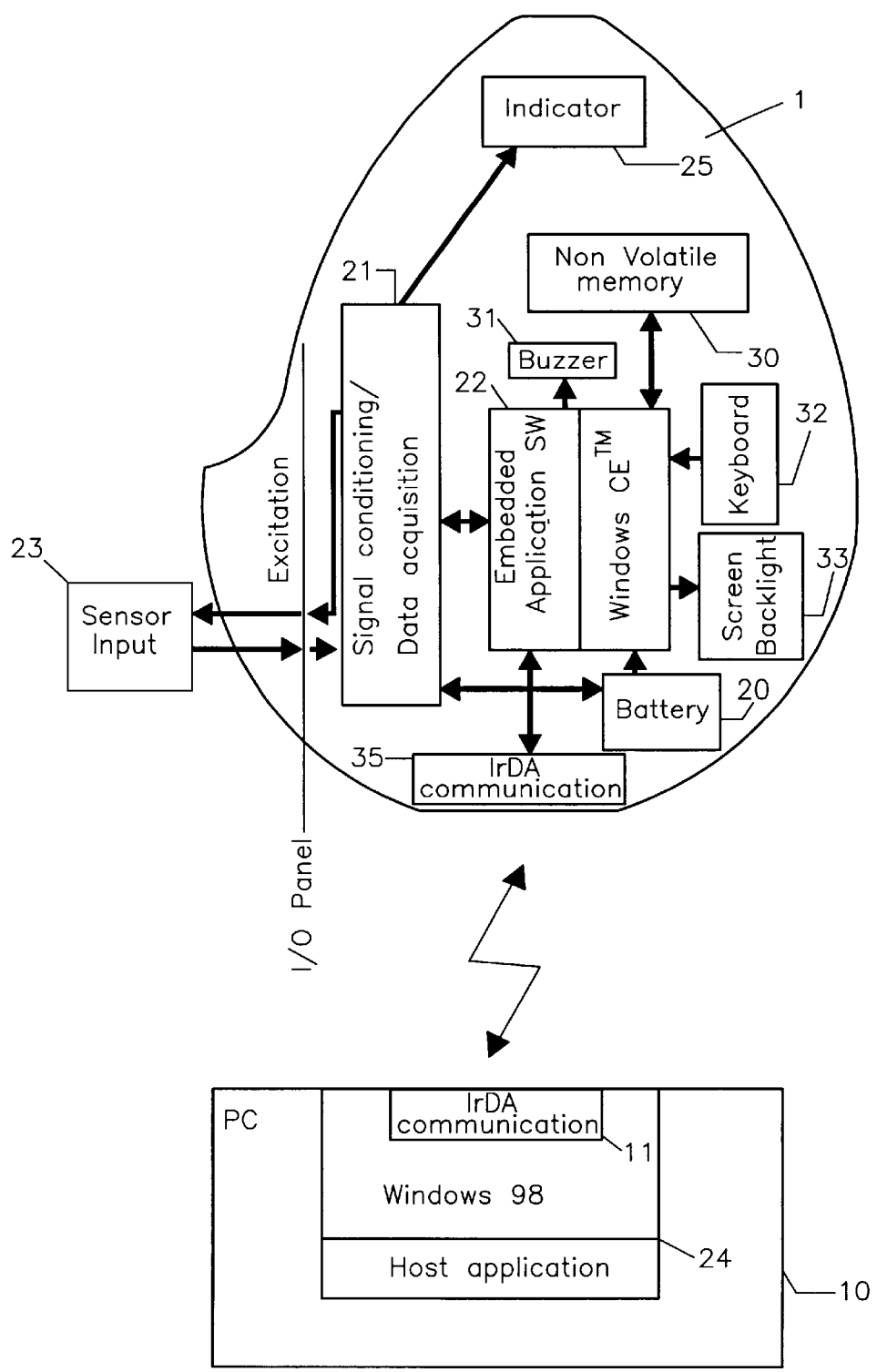
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21, the battery is coupled as well as to a non-real time processor 22 that runs the application. As disclosed in more detail below, real time processor 21 is a lower power processor which is used to sample data which is received from sensor input 23 by a sensor attached there to (not shown in this FIG.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Washington.

As further seen in this figure, recorder features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In the preferred embodiment the real time processor ("RTP") is the model PIC16LC67 from Microchip Technology Inc., Chandler, Ariz.; the non real time processor ("NRTP") is the model ElanSC400 from Advanced Micro Devices, Inc. Sunnyvale, Calif.; and non-volatile memory is the model Minicard AMMCL004AWP from Advanced Micro Devices, Inc. Sunnyvale, Calif.

Figure 3:
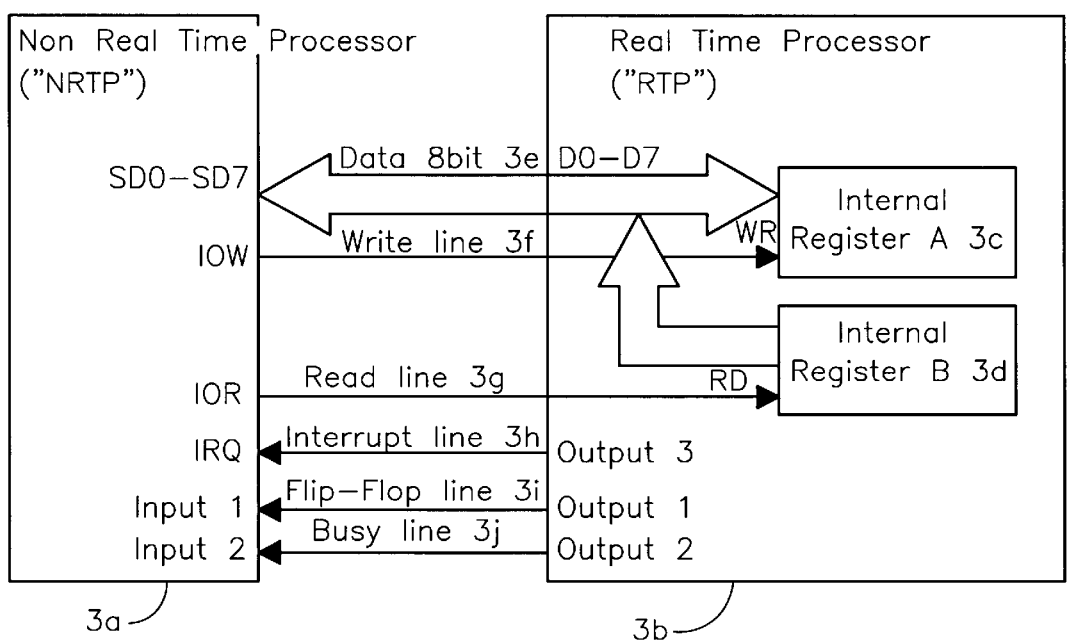
FIG. 3 shows the signal lines used for the communication between the two processors.

FIG. 3 shows the signal lines used for the communication between the two processors. As seen, NRTP and RTP communicate along the following lines: Data bus 3e transfers data (this term is used in its broadest meaning and may include values, commands, argument, information, etc.) between RTP and NRTP. In the preferred embodiment this is an 8 bit bus, although other sizes may be used. Write line 3f, driven by the NRTP, writes data into the internal register A 3c of the RTP. Read line 3g, driven by the NRTP, reads into the internal register B 3d of the RTP. Interrupt line 3h, is driven by the RTP to interrupt the NRTP and signify that a command is available on its internal register B 3d of the RTP. Flip-flop line 3i is driven by the RTP in order to "synchronize" the transfer between the two processors. The operation of flip-flop line 3i line in order to synchronize the communication between the two processors will be made more clear below, but the flip-flop basically functions as a signal, indicating to the NRTP that there is something which has been sent either from or to the RTP. Thus, flip-flop line 3i has two functions, the particular function provided depends upon where within the communication protocol or sequence you are: First, flip-flop may signal there is something to read in the internal register B of RTP. Secondly, flip flop may signal that the data that the NRTP wrote in the internal register A has been read. The busy line 3j driven by the RTP signals to the NRTP that the RTP is busy doing something and that is not able to communicate. It should be understood that the lines are shown as discrete individual pathways for communication, although a common communication data bus may be provided as a pathway of communication.

Whenever the NRTP 3a writes into the internal register A 3c, or when the NRTP 3a reads the internal register B 3d, an interrupt is generated in the RTP 3b. This interrupt ensures the RTP can accurately be aware of any access to those registers. The NRTP, in contrast, has no internal way of knowing that a valid data can be read on the internal register B 3d or that the data it wrote on the internal register A 3c has been read. The flip-flop line 3i makes this possible by giving a feedback of any read or write to the internal registers.

Busy line 3j is also important to the operation of the device. In the preferred embodiment the RTP is running a real time single task software; while the NRTP is running a non-real time multitasking operating system and application with priorities. Thus, communication with the RTP could be started by several tasks at the same time, creating confusion in the exchange of data between the processors. Busy line 3j prevents such confusion by giving feedback to the NRTP that a communication session is in progress.

Figure 5:
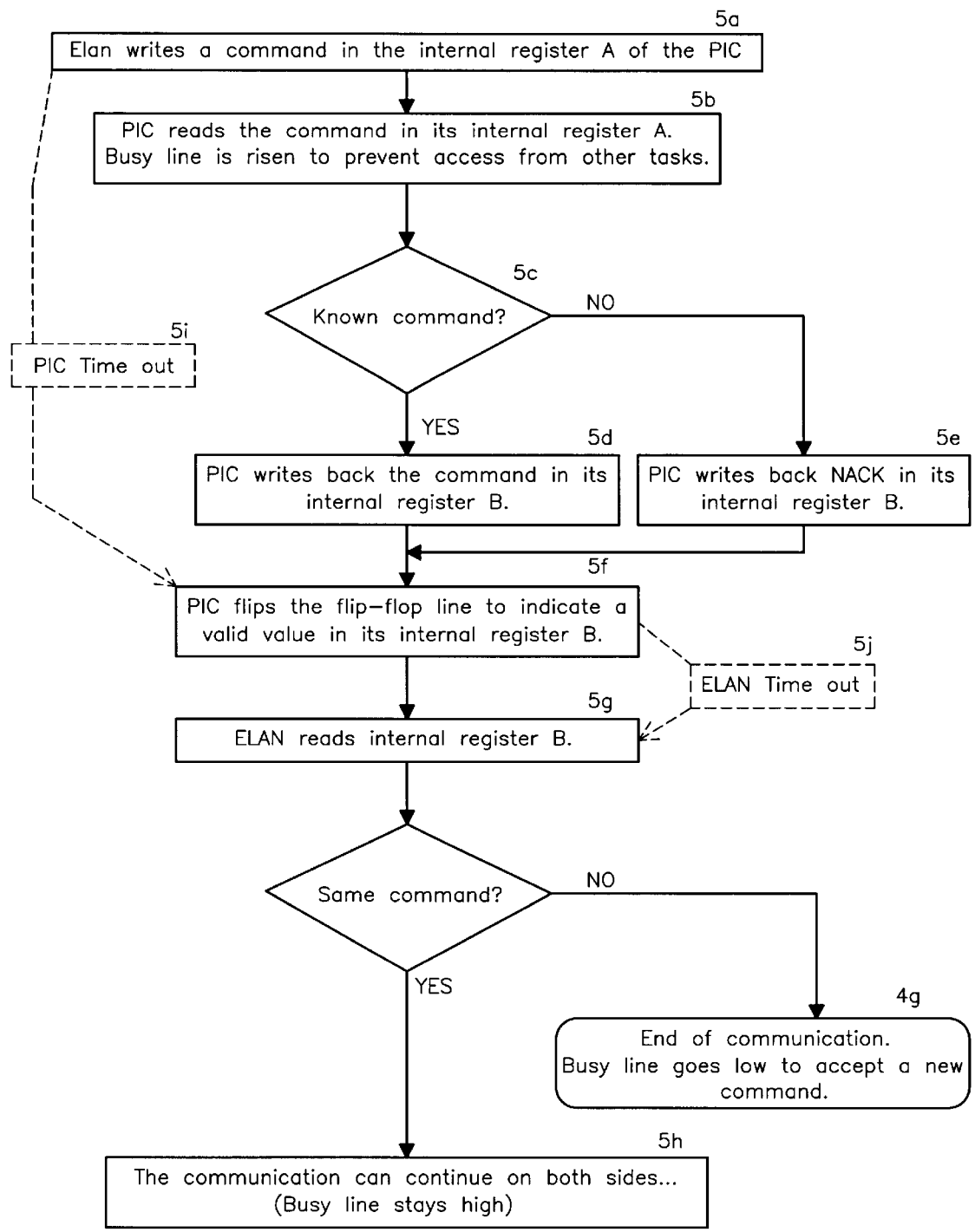
FIG. 5 shows the flowchart of the steps used in the module "Command from the ELAN to the PIC" depicted as 4c in FIG. 4.
Figure 6:
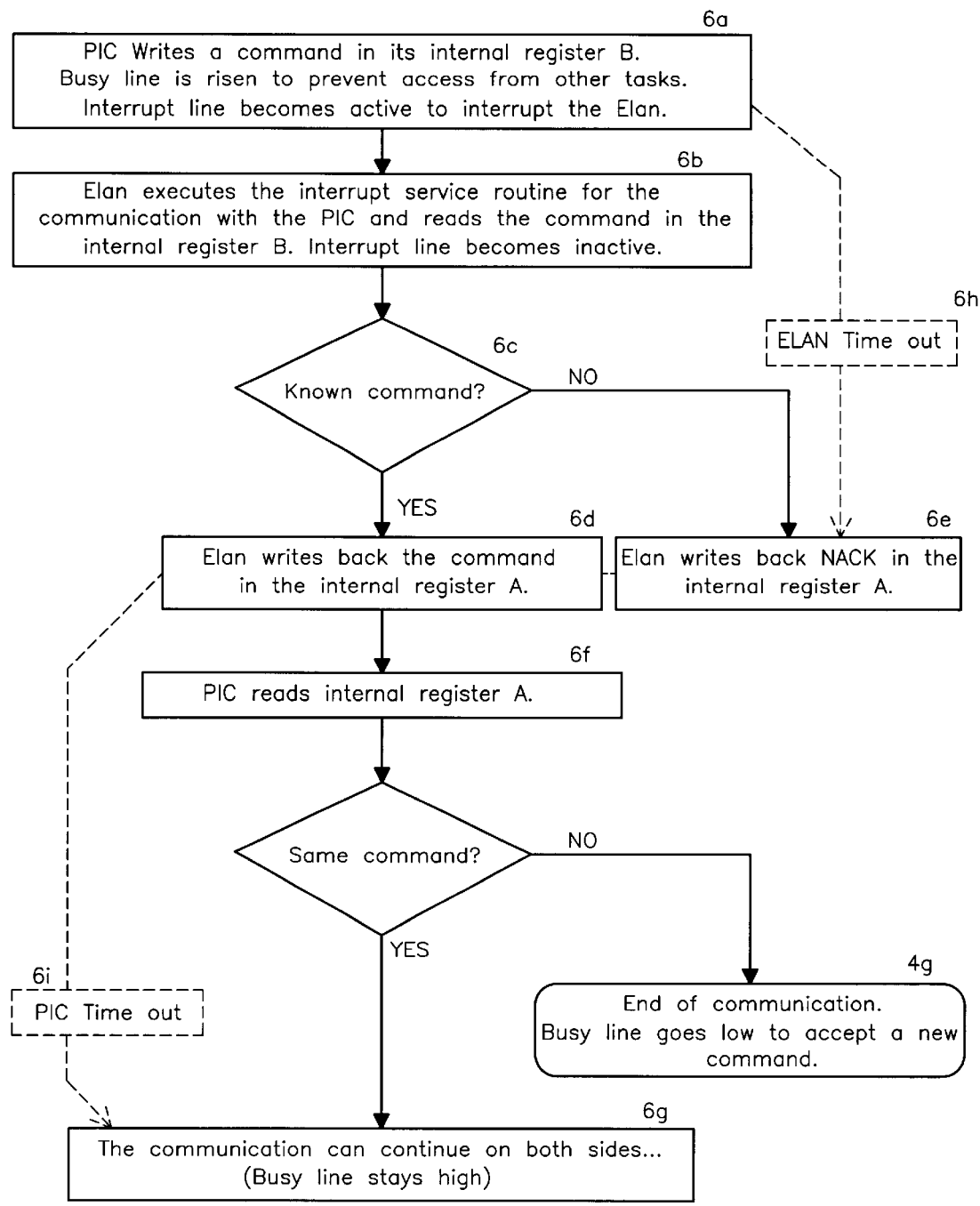
FIG. 6 shows the flowchart of module "Command from the PIC to the ELAN" seen as 4c in FIG. 4.
Figure 7:
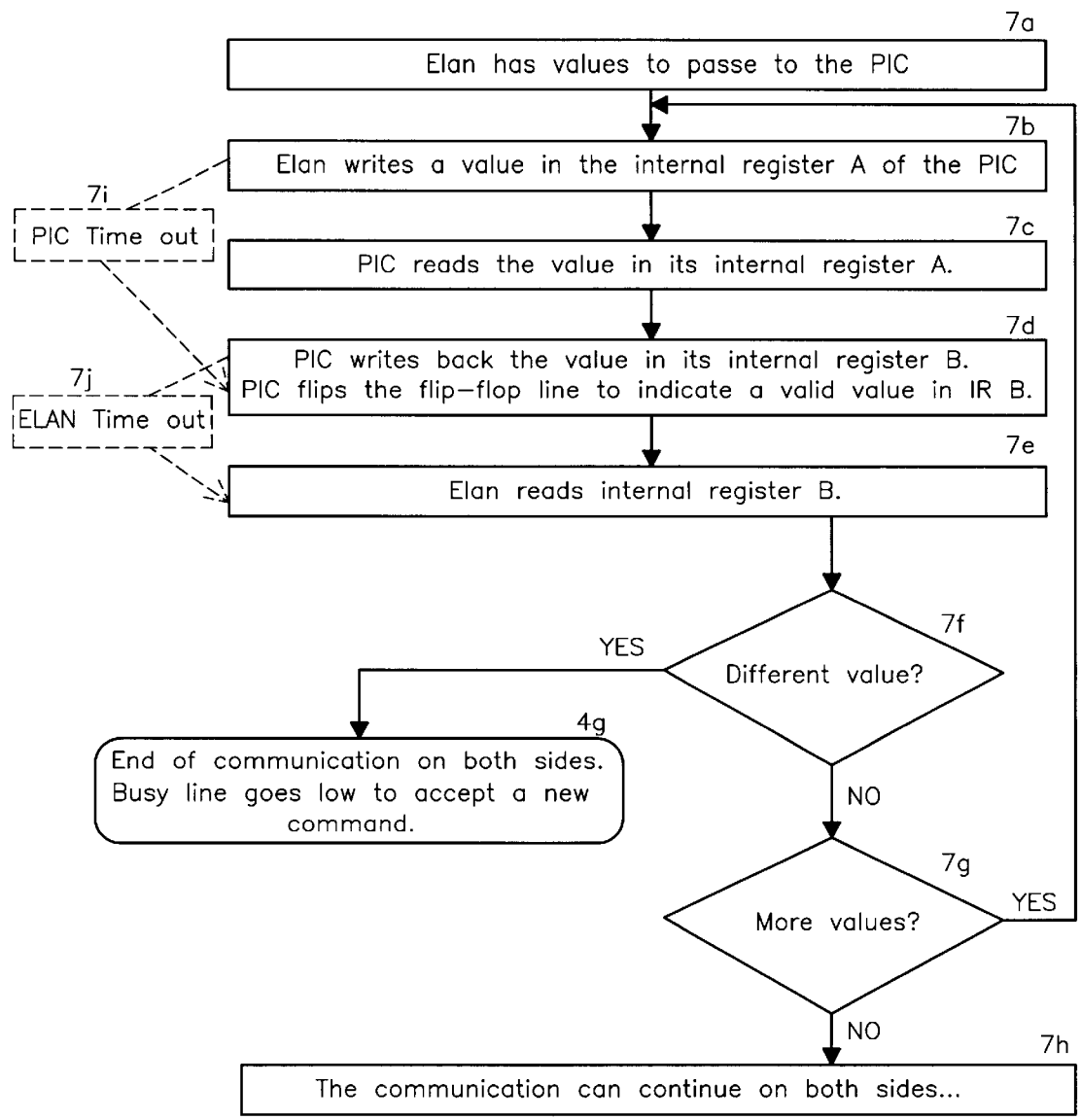
FIG. 7 shows the flowchart of module "Value from the ELAN to the PIC" depicted as 4e in FIG. 4.

The device further ensures reliable communication between the processors may occur through a time out feature. During communication, each processor checks that the other one responds in a certain range of time (i.e. before a certain time out). If the time out is exceeded the communication is considered failing. This feature is illustrated in FIGS. 5–7, shown below. In the preferred embodiment the response time of the RTP is reasonably fast (several microseconds) since it runs a single task. Therefore the RTP time out can be of 100 micro seconds. The latency on the NRTP side, on the other hand, can vary from several hundred micro seconds to milliseconds, since it runs a pre-emptive operating system. Nevertheless by experience, setting the NRTP time out at 20 milliseconds yields acceptable operation of the device. Of course, other values may also be selected, depending of what constitutes acceptable operation of the device, which may vary depending on the signals to be recorded.

Generally speaking, the time out is set as follows. When the NRTP returns an error due to a time out occurring prior to a responding communication from the RTP, then the device returns an error in the application, the application being a user application run on the NRTP. After such an error is detected the communication is again restarted. Should a preselected number of time outs be experienced, 5 in a row in the preferred embodiment, then the device disables itself and sends out a "service me". command to the user through the display.

Figure 4:
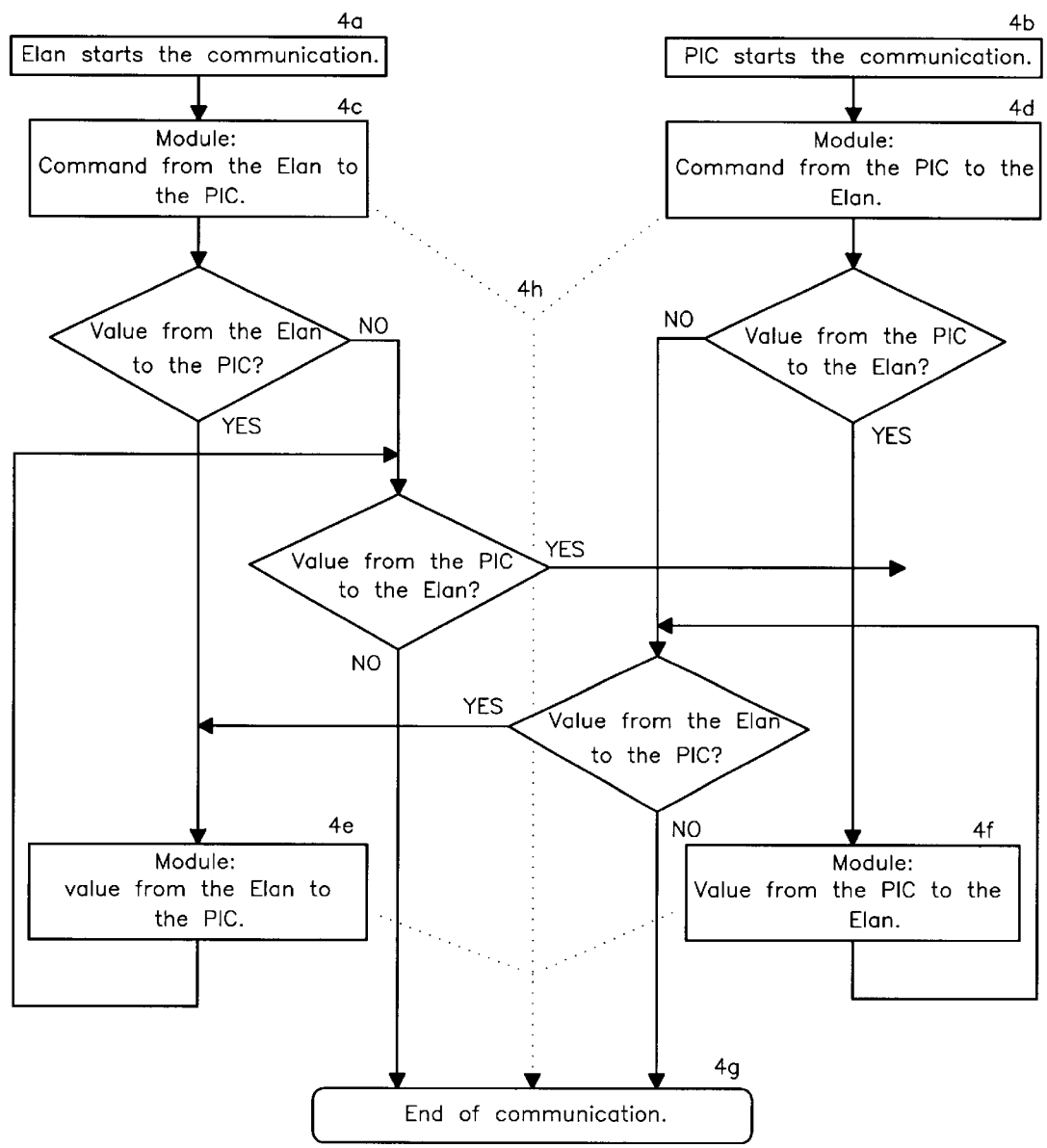
FIG. 4 depicts the flowchart of the communication protocol.

FIG. 4 depicts the flowchart of the communication protocol. The communication always starts by one of the processors sending data or a command to the other one; and then, according to the data or command, the two processors exchange values until the end of communication.

For simplicity, the communication can be divided into several modules.

If the NRTP (ELAN processor) starts the communication 4a, then it uses first the module "Command from the ELAN to the PIC" 4c. If the NRTP (ELAN processor) has then value(s) to passed to the PIC, then it will use the module "Value from the ELAN to the PIC" 4e until the NRTP (ELAN processor) has no more values. The RTP (PIC processor) can respond by giving back an expected amount values. The protocol uses then the module "Value from the PIC to the ELAN" 4f until all the values has been passed. The communication can now continue like this using these two last modules until there is no more value to exchange and the module "End of communication" 4g is reached.

If the RTP (PIC processor) starts the communication 4b, then it uses first the module "Command from the PIC to the ELAN" 4d. If RTP (PIC processor) has then value(s) to passed to the ELAN, then the RTP (PIC processor) will use the module "Value from the PIC to the ELAN" 4f until it has no more values. The NRTP (ELAN processor) can respond by giving back an expected amount values. The protocol then uses the module "Value from the ELAN to the PIC" 4e until all the values has been passed. The communication can now continue like this using these two last modules until there is no more value to exchange and the module "End of communication" 4g is reached.

Of course, in each module, the communication is checked to ensure it is working properly. This is done through the provision of the time out as well as the reading back to the processor of the data that processor sent to the other processor, discussed above. If any communication failure happens 4h, communication is ended 4g. Moreover, upon detection of a communication failure, several events may occur. On the NRTP (ELAN processor) side, the application gives a feedback to the user that the second processor is not responding. On the RTP (PIC processor) side, it can ignore the failure or force the NRTP (ELAN processor) to restart. A suitable method for initiating a restart may be seen in the patent application of the same inventors filed on this same day and entitled "Ambulatory Recorder Having a Communication Watchdog between Two Processors" (Our ref. P-8142 CIP #2).

As can be appreciated, there are many types of communication passed between the RTP (PIC processor) and the NRTP (ELAN processor). Below are two examples of communication between these processors. These are provided for illustration only and are not intended to be limiting.:

Example 1: The steps in the communication where the NRTP wants the sampled value of a pH channel:
1) Command from the NRTP (ELAN processor) to the RTP (PIC processor) using 4c: Read a channel.
2) Value from the NRTP (ELAN processor) to the RTP (PIC processor) using module 4e: Channel 1, for example.
3) Values from the RTP (PIC processor) to the NRTP (ELAN processor) 4f (e.g. i.e. channel 1 has a value reported as 1.425 mV).
4) End of communication using module 4g.

Example 2: The steps in the communication where the RTP wants to download its buffer of samples to non-volatile memory.
1) Command from the RTP (PIC processor) to the NRTP (ELAN processor) using module 4d: Download buffer to non-volatile memory.
2) Values from the RTP (PIC processor) to the NRTP (ELAN processor) using module 4f: 80 (Number of samples to download).
3) Value from the NRTP (ELAN processor) to the RTP (PIC processor) using module 4e: Acknowledge.
4) Values from the RTP (PIC processor) to the NRTP (ELAN processor) using module 4f: 80 (samples).
5) Value from the NRTP (ELAN processor) to the RTP (PIC processor) using module 4e:
6) Acknowledge (samples are saved).
7) End of communication using module 4g.

Thus, as seen, communication between the two processors may be facilitated through the series of modules shown in FIG. 4. Through these modules, a reliable and systematic method of communicating between the two processors may be fashioned and kept synchronized, even though the processors may be operating in differing time domains, i.e. a real time processor (RTP, e.g. the PIC Processor) and a non-real time processor (NRTP, e.g. the ELAN Processor).

FIG. 5 shows the flowchart of the steps used in the module "Command from the ELAN to the PIC" depicted as 4c in FIG. 4 As seen, at step 5a communication starts by the NRTP (ELAN processor) writing a command in the internal register A of the RTP (PIC processor). Next, as seen at step 5b, this causes, in turn, the RTP (PIC processor) to read that command in its internal register A. The RTP (PIC processor) at this time also rises a busy line (seen as 3j in FIG. 3) to prevent other attempts to write commands into it by other tasks being carried out in the NRTP(ELAN processor). At step 5c the RTP (PIC processor) checks then if the command is known. If it is a known command, then the RTP (PIC processor) will write back the same command in its internal register B, as seen at step 5d; if it is not a known command, then the RTP (PIC processor) write back at step 5e that the command is not acknowledged (abbreviated here as "NACK"). Regardless of whether the command is known or NACK, the RTP (PIC processor) proceeds to step 5f and flips the flip-flop line 3i (seen in FIG. 3) indicating that the register B of the RTP (PIC processor) can be read.

It is important that both processors recognize the same command as well as the data transferred because the ultimate reliability and accuracy of the device depend on it.

The NRTP (ELAN processor) is waiting for the flip-flop line 3i (seen in FIG. 3) to flip in a time less than the RTP (PIC processor) time out 5i. If the time required to flip the line exceeds a pre-selected allowed time, then a communication failure is deemed to occur. At this point the recorder may reset itself, a suitable method for initiating a restart may be seen in the patent application of the same inventors filed on this same day and entitled "Ambulatory Recorder Having a Communication Watchdog between Two Processors" (Our ref. P-8142 CIP #2).

As seen, at step 5g the NRTP (ELAN processor) reads the internal register B and checks the returned command. If the returned command is a NACK, then the communication stops (this is because the selected version of the RTP (PIC processor) does not know this new command, although other actions upon receipt of a NACK may be fashioned). As seen at step 5h, if the returned command is the same command, the RTP (PIC processor) knows how many values on both sides have to be exchanged and the communication can continue on both sides (busy line 3j of FIG. 3 stays high).

The RTP (PIC processor) surveys how long it takes to the NRTP (ELAN processor) to read back the command. This has to happen before the NRTP (ELAN processor) time out or else we get a communication failure. At this point any of the above-mentioned actions may be initiated (e.g. device reset.)

FIG. 6 shows the flowchart of module "Command from the PIC to the ELAN" seen as 4c in FIG. 4. As seen in step 6a communication begins by the RTP (PIC processor) writing a command in its internal register B. the RTP (PIC processor) rises the busy line to prevent other attempt to write command into it by other tasks and active the interrupt line. Next, at step 6b the NRTP (ELAN processor) is interrupted and executes an interrupt service routine, which will read the command in the internal register B. At this time the RTP (PIC processor) also notices the read and the interrupt line becomes inactive. Next, at step 6c the NRTP (ELAN processor) checks if the command is known. If the command is a known command, then the NRTP (ELAN processor) proceeds to step 6d and writes back the same command in the internal register A. If the command is not a known command, then the NRTP (ELAN processor) proceeds to step 6e and writes back a NACK (non-acknowledge command signal). The RTP (PIC processor) waits for that event in a time less than the NRTP (ELAN processor) time out, seen in step 6h. If it exceed to allowed time, we get a communication failure. At this point any of the above-mentioned actions may be initiated (e.g. device reset.) Continuing now at step 6f, the RTP (PIC processor) reads its internal register A and checks the return command. If it is a NACK (non-acknowledge command signal), then the communication stops (this version of the application on the NRTP (ELAN processor) does not know this new command) whereupon the device proceeds to step 4g. If it is the same command, the NRTP (ELAN processor) knows how many values on both sides have to be exchanged and the communication can continue, seen as step 6g.

Figure 8:
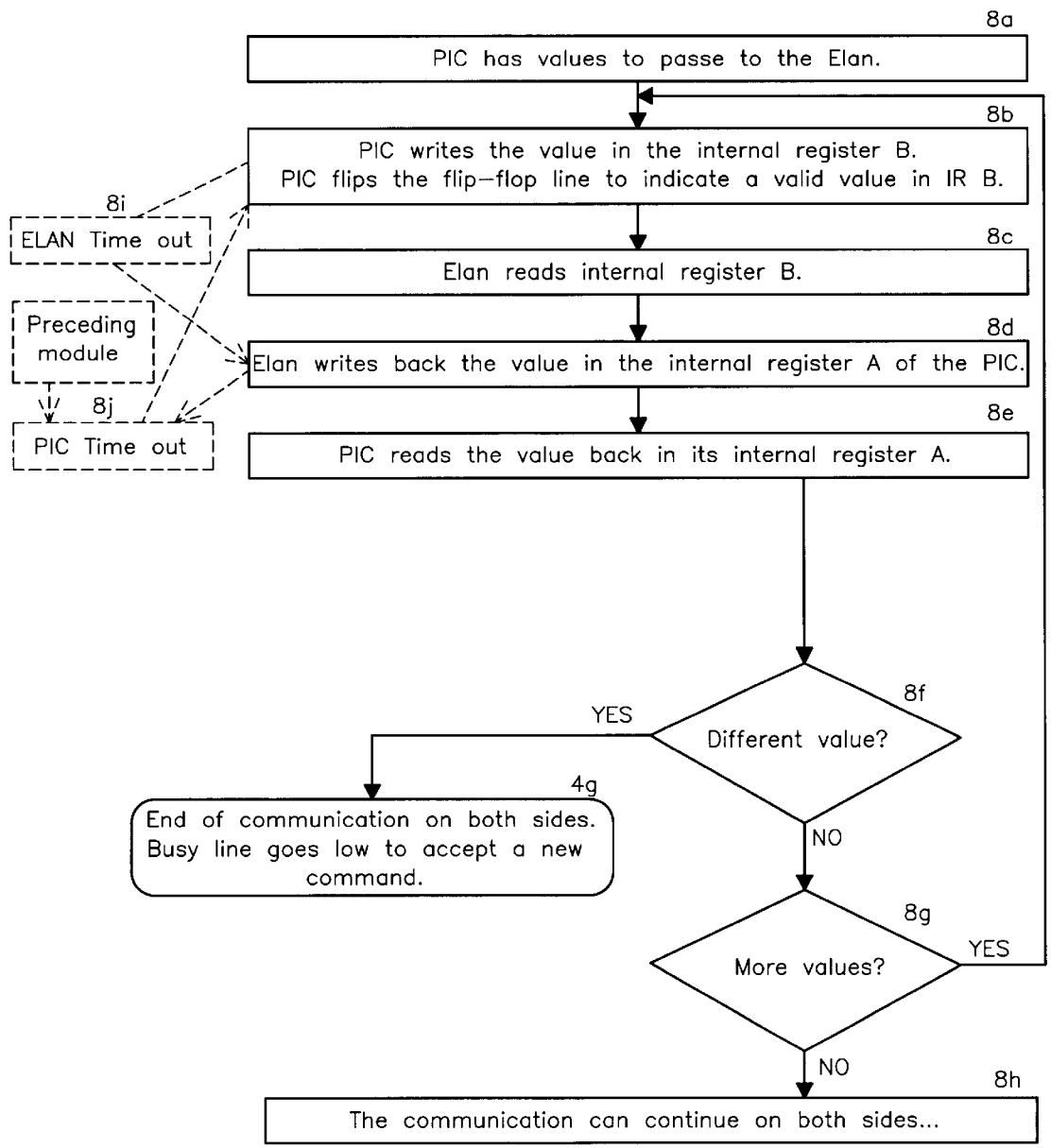
FIG. 8 shows the flowchart of module "Value from the PIC to the ELAN" depicted as 4f in FIG. 4.

Depending on the command, the RTP (PIC processor) will pass a value (module 4f Value from the PIC to the ELAN and discussed in more detail in FIG. 8), if it is the case, the NRTP (ELAN processor) surveys how long it takes to the RTP (PIC processor) to perform the next task 6i. This has to happen before the RTP (PIC processor) time out or else we get a communication failure. At this point the recorder may reset itself, a suitable method for initiating a restart may be seen in the patent application of the same inventors filed on this same day and entitled "Ambulatory Recorder Having a Communication Watchdog between Two Processors" (Our ref. P-8142 CIP #2).

FIG. 7 shows the flowchart of module "Value from the ELAN to the PIC" depicted as 4e in FIG. 4. As seen, at step 7a the NRTP (ELAN processor) has one or more values to passed to the RTP (PIC processor). Next at step 7b the NRTP (ELAN processor) writes a value in the internal register A of the RTP (PIC processor). As seen before that causes an interrupt inside the RTP (PIC processor) which will read the value (step 7c) the RTP (PIC processor) writes back the same value in its internal register B and flips the flip-flop line 3l indicating that the register A has been read (step 7d). The NRTP (ELAN processor) is waiting for that line to flip in a time less than the RTP (PIC processor) time out (step 7i). If it exceed to allowed time, we get a communication failure. At this point any of the above-mentioned actions may be initiated (e.g. device reset.) The NRTP (ELAN processor) reads the internal register B and checks the return value (step 7f). If it is different the communication stops (bad transfer of value) and the device proceeds to the step 4g depicted here and in FIG. 4. If it is the same, the NRTP (ELAN processor) checks if it has more values to passed (step 7g). If it is the case it returns to state 7b. If not the communication can continue according to the protocol (step 7h). The RTP (PIC processor) surveys how long it takes to the NRTP (ELAN processor) to read back the value. This has to happen before the NRTP (ELAN processor) time out or else we get a communication failure. At this point any of the above-mentioned actions may be initiated (e.g. device reset).

FIG. 8 shows the flowchart of module "Value from the PIC to the ELAN" depicted as 4f in FIG. 4. As seen, at step 8a the RTP (PIC processor) has one or more values to passed to the NRTP (ELAN processor). The RTP (PIC processor) writes a value in its internal register B and flips the flip-flop line 3l (seen in FIG. 3) indicating that the register B can been read (step 8b). The NRTP (ELAN processor) is waiting for that line to flip in a time less than the RTP (PIC processor) time out (step 8j). If it exceeds to allowed time, then a communication failure is deemed to occur. The NRTP (ELAN processor) reads the internal register B and writes back the same value in the internal register A (step 8c). As seen before that causes an interrupt inside the RTP (PIC processor) which will read back the value (step 8e). The RTP (PIC processor) surveys how long it takes for the NRTP (ELAN processor) to write back the value (step 8*i*). This has to happen before the NRTP (ELAN processor) time out or else a communication failure is deemed to occur. The RTP (PIC processor) checks the return value (step 8*f*). If it is different the communication stops (bad transfer of value) (step 4*g* shown here as well as in FIG. 4). If it is the same, the RTP (PIC processor) checks if it has more values to pass (step 8*g*). If it has more values to pass, then it returns to state 8*b* and the NRTP (ELAN processor) waits for the next value in a time less than the RTP (PIC processor) time out 8*j*. If it exceeds to allowed time, then a communication failure is deemed to occur. If there are no more values to pass, the communication can continue according to the protocol 8*h*.

As discussed above, at any point where there is a communication failure, any of the above-mentioned actions may be initiated (e.g. device reset).

Figure 9:
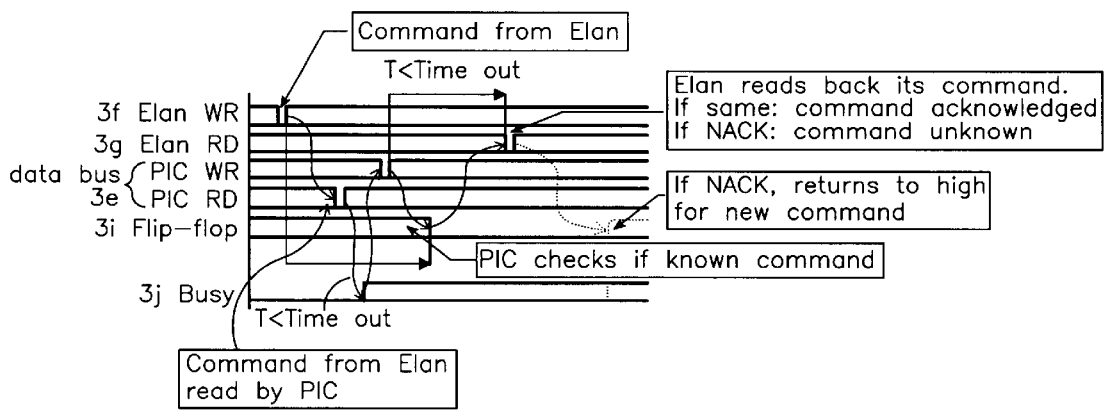
FIG. 9 depicts the status of the lines between the RTP processor (PIC) and the NRTP processor (ELAN) as a transfer of command is made from the ELAN to the PIC.

FIGS. 9–12 depict examples of the device operation and particularly of the status of the lines between the PIC and the ELAN as commands are sent between the processors. FIG. 9 depicts the status of the lines between the "RTP (PIC processor)" and the "NRTP (ELAN processor)" as a transfer of command is made from the "NRTP (ELAN processor)" to the "RTP (PIC processor)". As seen, when the "NRTP (ELAN processor)" wants to begin a communication or transaction with the "RTP (PIC processor)" it writes the command on "ELAN WR" corresponding with line 3*f* (referring to FIG. 3). Thereafter, this command is read by the "RTP (PIC processor)" along the PIC RD line (depicted in FIG. 3 as data bus 3*e*). Once the "RTP (PIC processor)" reads the command from the "NRTP (ELAN processor)" the busy line 3*j* is set high and the "RTP (PIC processor)", thereafter, writes back the command on data bus 3*e* to the "NRTP (ELAN processor)". Thereafter, the "RTP (PIC processor)" checks if it is a known command and, if yes, sets the flip-flop line 3*l* low. Subsequent to that the "NRTP (ELAN processor)" again reads back from the "RTP (PIC processor)" the command sent on line 3*g*. As seen, if the command is read back as the same as that sent, then the "NRTP (ELAN processor)" notes the command as acknowledged and communication may begin. If the command read back is not the same, then it is defined as a NACK (not acknowledged) and it means the "RTP (PIC processor)" cannot perform the command and a communication failure is deemed to occur. At this point, any of the above-mentioned actions may be initiated (e.g. device reset) If the command read back by the "NRTP (ELAN processor)" is the same, however, communication may occur and the "NRTP (ELAN processor)" may present its first argument.

Figure 10:
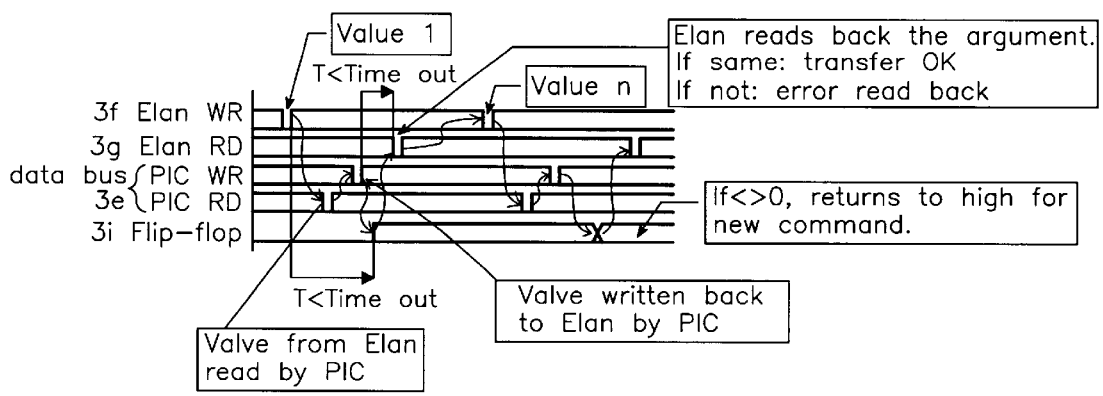
FIG. 10 depicts the status of the lines between the RTP processor (PIC) and the NRTP processor (ELAN) as an argument is presented from the ELAN to the PIC.

FIG. 10 depicts the status of the lines between the "RTP (PIC processor)" and the "NRTP (ELAN processor)" as an argument is presented from the "NRTP (ELAN processor)" to the "RTP (PIC processor)". As seen, a value 1 is written by the "NRTP (ELAN processor)" on line 3*f*. This is subsequently read by the "RTP (PIC processor)" from the "NRTP (ELAN processor)". As illustrated, this occurs on line PIC RD which is within the data bus 3*e* (referring to FIG. 3). Thereafter, this value is written by the "RTP (PIC processor)" back to the "NRTP (ELAN processor)" on line PIC WR. Thereafter, the flip-flop is set high. Shortly thereafter, the "NRTP (ELAN processor)" reads along line 3*g* the writing from the "RTP (PIC processor)". If what the "NRTP (ELAN processor)" reads back is the same then the transfer is okay and communication may occur. This is shown in this figure as a subsequent value written by the "NRTP (ELAN processor)" on line 3*f* back to the "RTP (PIC processor)", seen here as value N. At this point the steps of communication are again repeated such that subsequent values from the "NRTP (ELAN processor)" may be read and transferred to the "RTP (PIC processor)". On the other hand, if the value read back from the "RTP (PIC processor)", to the "NRTP (ELAN processor)" on line 3*g* is incorrect a NACK is defined and a communication failure is deemed to occur. Although not shown in this figure, during the transfer of values or arguments from the "NRTP (ELAN processor)" to the "RTP (PIC processor)" the busy line 3*j* is always set high.

Figure 11:
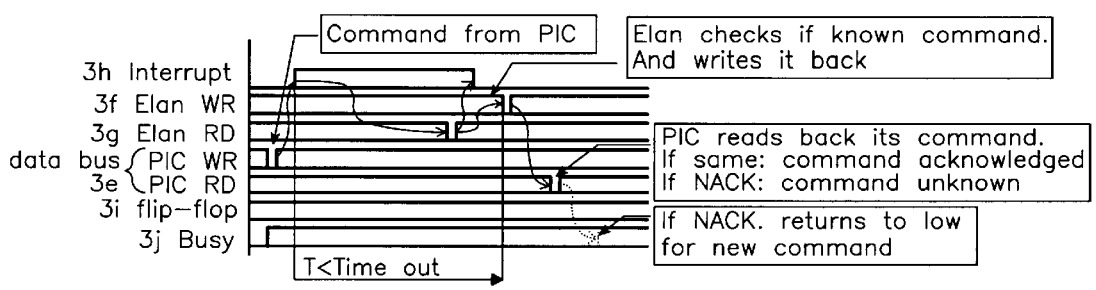
FIG. 11 depicts the status of the lines between the RTP processor (PIC) and the NRTP processor (ELAN) when a command is transferred from the PIC to the ELAN.

FIG. 11 depicts the status of the lines between the "RTP (PIC processor)" and the "NRTP (ELAN processor)" when a command is transferred from the "RTP (PIC processor)" to the "NRTP (ELAN processor)". When the "RTP (PIC processor)" wants to start a communication or transaction, the "RTP (PIC processor)" must interrupt the "NRTP (ELAN processor)". This is sent as a command seen at line PIC WR which, as discussed above, is part of data bus 3*e* shown in FIG. 3. This command, sent from the "RTP (PIC processor)", sets the interrupt high, seen here as line 3*h*. Once this interrupt is set high the "NRTP (ELAN processor)" will read the command upon servicing the interrupt, at which point it reads the command and checks to determine if it is a known command. Once the command is read the "NRTP (ELAN processor)" sets the interrupt low and the "NRTP (ELAN processor)" writes the command back on line 3*f* to the "RTP (PIC processor)". Thereafter, the "RTP (PIC processor)" reads this returned command from the "NRTP (ELAN processor)" at line PIC RD which, as discussed above, is part of data bus 3*e*. If the command read back by the "RTP (PIC processor)" is the same, the command is acknowledged and communication may begin. Once the "RTP (PIC processor)" begins to read a command the busy line 3*j* is set high to inhibit further communication from the "NRTP (ELAN processor)" to the "RTP (PIC processor)". If the command read back by the "RTP (PIC processor)" is not the same then a NACK is signaled and a communication failure is deemed to occur. As seen, when a NACK is detected the busy line may be returned low.

As also seen in this FIG., once the "RTP (PIC processor)" writes the command and triggers the interrupt it sets a timing window such that the "RTP (PIC processor)" waits for the command to be written back to it from the "NRTP (ELAN processor)" for only a limited amount of time. If the "NRTP (ELAN processor)" does not write back to the "RTP (PIC processor)" the command sent back by the "RTP (PIC processor)" within this limited amount of time a communication failure is deemed to occur.

Figure 12:
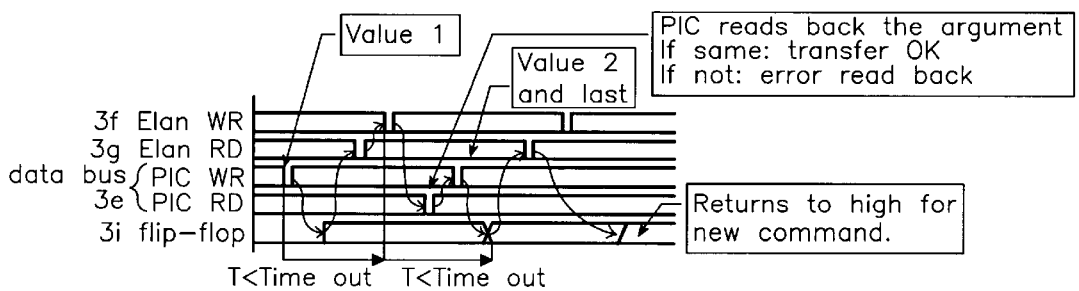
FIG. 12 depicts the status of the lines between the RTP processor (PIC) and the NRTP processor (ELAN) during the transfer of a value from the PIC to the ELAN.

FIG. 12 depicts the status of the lines between the "RTP (PIC processor)" and the "NRTP (ELAN processor)" during the transfer of a value from the "RTP (PIC processor)" to the "NRTP (ELAN processor)". As seen, the "RTP (PIC processor)" begins the transfer of value by writing along PIC WR line (which is part of the data bus 3*e* shown in FIG. 3). Shortly after writing on this line the "RTP (PIC processor)" also flop-flops line 3*i* high. The "NRTP (ELAN processor)", thereafter, reads what the "RTP (PIC processor)" has written through line 3*g* and again writes back this value to the "RTP (PIC processor)" at line 3*f*. Thereafter, if the "RTP (PIC processor)" reads back the argument from the "NRTP (ELAN processor)" which was the same written by the "RTP (PIC processor)" at line PIC WR then the transfer is deemed to be okay and further communication may be continued. Otherwise, an error may be read back and a communication failure may be deemed to occur. As shown, if a valid argument has been read back, then a second value is written at "RTP (PIC processor)" line PIC WR. Flip-flop 3*l* is, thereafter, set low and the process then again continues. The processor, thereafter, continues until all values are exchanged and further communication is ended.

As discussed above, at any point where there is a communication failure, any of the above-mentioned actions may be initiated (e.g. device reset).

FIG. 13 is a back view of the recorder shown in FIG. 2. As seen, recorder 1 features a belt loop 74 which may be used to mount the recorder to a patient using either the patient's belt or the shoulder strap.

FIG. 14 is a side view of recorder shown in FIG. 2. As further seen in this view, housing 55 features a pair of sensor inputs 75 and 76. In the preferred embodiment, input 75 is for a pH catheter while input 76 is for a pressure measuring catheter.

Thus, the present invention concerns an ambulatory recordings device and system for medical and especially diagnostic purposes, and an ambulatory recorder device and system having synchronized communication between two processors. The recorder preferably features two processors which are of differing architectures—the first processor being a real time processor (RTP) which handles the sampling function, the second processor being a non real time (NRTP) processor which handles the operating system function. It should be understood, however, that while two different types of processors are illustrated, the invention may also be used with two identical processors, such as two real time processors, where only one of the processors operates while needed, such as to control the device interface and/or operating system. In this manner the invention, thus, ensures communication between even two identical processors will be dependable, reliable and accurate. The invention further includes a protocol for communication between the two processors which permits the processors to have synchronized and safe communication. Further, the invention may also be used within a single mixed signal mixed processor, if desired as well as in a recorder featuring three or more processors. It is contemplated that various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory medical recording system, comprising:
   a medical sensing catheter;
   a medical data recorder coupled with the medical sensing catheter, the medical data recorder comprising;
      a first processor;
      a second processor;
      wherein the first processor and the second processor communicate along at least one communication line, the second processor having means for writing data along the least one communication line, the second processor further having means for setting a time out windows, the time out window beginning at the writing of data along the least one communication line.

2. An ambulatory medical recording system according to claim 1, wherein the first processor is a real time processor RTP and the second processor is a non real-time processor NRTP.

3. An ambulatory medical recording system according to claim 1, wherein the at least one communication line comprises a data bus.

4. An ambulatory medical recording system according to claim 2, further comprising the NRTP having means for writing to the RTP;

the RTP having means for reading the writing from the NRTP;

the RTP having means for writing back to the NRTP what the RTP has read from the NRTP; and the NRTP having means for reading what the RTP has written back.

5. An ambulatory medical recording system according to claim 4, wherein the means for writing to the RTP from the NRTP further comprises means for setting a timing window, the timing window defining the lime period in which the RTP must respond back to the NRTP before the NRTP retries writing to the RTP.

6. An ambulatory medical recording system according to claim 5, wherein the NRTP further comprises means for counting the number of times in a row the NRTP retries writing to the RTP due to the timing window lapsing; and means for sending out a message to the user when the number of times in a row the NRTP retries writing to the RTP due to the timing window lapsing exceeds a preselected number.

7. An ambulatory medical recording system according to claim 4, wherein means for reading the writing from the NRTP to the RTP further comprises means for setting a busy signal along the at least one communication line between the RTP and the NRTP.

8. An ambulatory medical recording system according to claim 4, wherein the RTP has means for writing back to the NRTP what the RTP has read from the NRTP, and further comprises means for signaling to the NRTP that the RTP has written data which the NRTP should read.

9. An ambulatory medical recording system according to claim 8, wherein the means for signaling to the NRTP that the RTP has written data which the NRTP should read comprises a flip flop moveable from a high state to a low state and back to a high state again.

10. A method of communicating between a NRTP and a RTP in a medical data recorder comprising:

the NRTP writing first data alone a first line to the RTP;

the RTP reading the first data along the first line from the NRTP;

the RTP writing second data along a second line to the NRTP and signaling to the NRTP that there is data to be read along the second line; and the NRTP reading the second data along the second line from the RTP;

a method of communicating between a NRTP and a RTP in a medical data recorder, wherein the first processor is a real time processor RTP and the second processor is a non real-time processor NRTP;

wherein the step of the RTP reading the first data along the first line from the NRTP further comprises setting a busy signal along a busy signal line between the RTP and the NRTP, and wherein the NRTP will not begin additional task communication with the RTP while the busy signal is present.

11. An ambulatory medical recording system, comprising:
   a medical sensing catheter;
   a medical data recorder coupled with the medical sensing catheter, the medical data recorder comprising:
      a first real time processor RTP;
      a second processor;
      wherein the RTP has means for writing data along a line of communication to the second processor, the RTP further having means for signaling to the second processor that the RTP has written data along the line of communication the second processor.

12. An ambulatory medical recording system according to claim 11, wherein the communication line comprises a data bus.

13. An ambulatory medical recording system according to claim 11, wherein:
the second processor has means for writing to the RTP;
the RTP has means for reading the writing from the second processor and means for writing back to the second processor what the RTP has read from the second processor;
the second processor has means for reading what the RTP has written back.

14. An ambulatory medical recording system according, to claim 13, wherein the means for writing to the RTP from the second processor further comprises means for setting a timing window, the timing window defining the time period in which the RTP must respond back to the second processor before the second processor retries writing to the RTP.

15. An ambulatory medical recording system according to claim 14, wherein the second processor further comprises means for counting the number of limes in a row the second processor retries writing to the RTP due to the timing windows lapsing, and means for sending out a message to the user when the number of times in a row the second processor retries writing to the RTP due to the timing window lapsing exceeds a preselected number.

16. An ambulatory medical recording system according to claim 13, wherein means for reading the writing from the second processor to the RTP further comprises means for setting a busy signal along the at least one communication line between the RTP and the second processor.

17. An ambulatory medical recording system according to claim 13, wherein the RTP further comprises means for writing back to the second processor what the RTP has read from the second processor and means for signaling to the second processor that the RTP has written data which the second processor should read.

18. An ambulatory medical recording system according to claim 17, wherein the means for signaling to the second processor that the RTP has written data which the second processor should read comprises a flip flop moveable from a high state to a low state and back again to a high state.

19. An ambulatory medical recording system according to claim 18, wherein the second processor is a non real time processor NRTP.

20. An ambulatory medical recording system comprising:
a medical sensing catheter;
a medical data recorder coupled with the medical sensing catheter, the medical data recorder comprising:
a first processor;
a second processor;
wherein the first processor and the second processor communicate along at least one communication line, the second processor having means for determining whether the first processor may have data communicated thereto from the second processor.

21. An ambulatory medical recording system according to claim 20, wherein the means for determining whether the first processor may have data communicated to it from the second processor comprises a flip flop.

22. An ambulatory medical recording system according to claim 20, the second processor further having means for setting a time out window starting from the writing of data along the least one communication line.

23. An ambulatory medical recording system according to claim 20, wherein the first processor is a real time processor RTP and the second processor is a non real-time processor NRTP.

24. A ambulatory medical recording system according to claim 20, wherein the at least one communication line comprises a first line of communication and a second line of communication.

25. An ambulatory medical recording system according to claim 20, wherein the at least one communication line comprises a data bus.

26. An ambulatory medical recording system according to claim 20, wherein:
the second processor includes means for writing to the first processor;
the first processor includes means for reading the writing from the second processor;
the first processor having means for writing back to the second processor what the first processor has read from the second processor; and
the second processor having means for reading what the first processor has written back.

27. An ambulatory medical recording system according to claim 26, wherein the means for writing to the first processor from the second processor further comprises means for setting a timing window, the timing window defining the time period in which the first processor must respond back to the second processor before the second processor retries writing to the first processor.

28. An ambulatory medical recording system according to claim 27, wherein the second processor further comprises means for counting the number of times in a row the second processor retries writing to the first processor due to the timing window lapsing; and means for sending out a message to the user when the number of times in a row the second processor retries writing to the first processor due to the timing window lapsing exceeds a preselected number.

29. An ambulatory medical recording system according to claim 26, wherein the means for reading the whiting from the second processor to the first processor further comprises means for setting a busy signal along the at least one communication line between the first processor and the second processor.

30. An ambulatory medical recording system according to claim 26, wherein the first processor includes means for writing back to the second processor what the first processor has read from the second processor and means for signaling to the second processor that the first processor has written data which the second processor should read.

31. An ambulatory recorder according to claim 30, further comprising means for mounting the ambulatory recorder to a patient.

32. An ambulatory recorder according to claim 31, wherein the mounting means further comprises a loop configured for a belt or a shoulder strap to be inserted theretrough.

33. An ambulatory recorder according to claim 20, wherein the medical sensing catheter comprises a pH sensing catheter.

* * * * *

UNITED STATES PATENT AND TRADEMARK OFFICE
CERTIFICATE OF CORRECTION

PATENT NO.  : 6,245,013 B1
DATED       : June 12, 2001
INVENTOR(S) : Minoz et al.

It is certified that error appears in the above-identified patent and that said Letters Patent is hereby corrected as shown below:

Column 3,
Line 35, change "in this figure" to -- in figure 1A, --.

Column 11,
Line 15, change "recordings" to -- recording --.

Column 12,
Line 12, change "lime" to -- time --.
Line 40, change "alone" to -- along --.

Column 13,
Line 24, change "limes" to -- times --.

Column 14,
Line 7, change "A" to -- An --.
Line 43, change "whiting" to -- writing --.
Line 60, change "theretrough" to -- therethrough --.

Signed and Sealed this

Twenty-seventh Day of May, 2003

JAMES E. ROGAN
*Director of the United States Patent and Trademark Office*